United States Patent [19]
Thörnberg

[11] Patent Number: 5,671,738
[45] Date of Patent: Sep. 30, 1997

[54] MEDICAL ENVIRONMENT INTERFACE

[75] Inventor: Benny Thörnberg, Sundsvall, Sweden

[73] Assignee: Regam Medical Systems International AB, Sundsvall, Sweden

[21] Appl. No.: 244,240

[22] PCT Filed: Nov. 25, 1992

[86] PCT No.: PCT/SE92/00812

§ 371 Date: May 24, 1994

§ 102(e) Date: May 24, 1994

[87] PCT Pub. No.: WO93/10709

PCT Pub. Date: Jun. 10, 1993

[30] Foreign Application Priority Data

Nov. 29, 1991 [EP] European Pat. Off. .............. 91850298

[51] Int. Cl.$^6$ ...................................................... A61B 5/05
[52] U.S. Cl. ...................... 128/653.1; 600/134; 128/89.7; 128/908
[58] Field of Search ...................... 128/653.1, 897, 128/898, 630, 4, 6, 908; 364/413.02, 413.13, 413.14, 413.28, 413.06; 600/132, 134; 607/63

[56] References Cited

U.S. PATENT DOCUMENTS

| | | | |
|---|---|---|---|
| 4,384,775 | 5/1983 | Hosoda | 128/6 |
| 4,473,841 | 9/1984 | Murakoshi et al. | 128/6 |
| 4,706,118 | 11/1987 | Kato et al. | 356/98 |
| 4,742,831 | 5/1988 | Silvian | 128/696 |
| 4,853,772 | 8/1989 | Kikuchi | 128/4 |
| 4,868,647 | 9/1989 | Uehara et al. | 128/4 |
| 4,963,903 | 10/1990 | Cane | 354/81 |
| 5,125,410 | 6/1992 | Misono et al. | 128/908 |
| 5,139,021 | 8/1992 | Sekii et al. | 128/908 |
| 5,174,293 | 12/1992 | Hagiwara | 128/908 |
| 5,309,918 | 5/1994 | Schraag | 128/908 |
| 5,400,792 | 3/1995 | Hoebel et al. | 128/670 |

*Primary Examiner*—Brian L. Casler
*Attorney, Agent, or Firm*—Young & Thompson

[57] ABSTRACT

The present invention provides a method and an apparatus to facilitate feeding of electric signals, achieved in a defined area of medical electric environment, to and from auxiliary equipment, specifically a so called Personal Computer (PC), without the necessity that such auxiliary equipment fulfill the requirements necessary for use within the area of medical electric environment. The apparatus includes an isolation device having its own power supply which is approved for the medical electric environment according to the International Standard IEC 601-1, an electronic buffering device connected to a CCD sensor and multiwire cables between the auxiliary equipment and the isolation device and the buffering device and the isolation device, respectively, facilitating parallel signal communication, whereby the isolation device includes a number of electromagnetic and/or optoelectric interfaces corresponding to the number of wires connecting the CCD sensor and the auxiliary equipment positioned in an area of non-medical electric environment.

14 Claims, 3 Drawing Sheets

MEDICAL ENVIRONMENT INTERFACE

The present invention relates to a method and an apparatus for electric safety of medical electric or electronic equipment and specifically for the safe electric protection of equipment for electronic dental diagnostic radiology by defining one environment for the medical electric equipment and another environment for other simultaneously connected auxiliary equipment and using an intermediate electrically approved insulating unit forming a link between the two environments.

BACKGROUND OF THE INVENTION

In recent days the development of the Charge Coupled Device (CCD) normally utilized for example in video camera technique also has made it possible to apply such devices for radiology. In dental X-ray examination this is a very advantageous technique as the dental application is very easy adopted to this new branch of art. In the dental intraoral application there is only need for fairly small X-ray detector surfaces and consequently CCD sensors of reasonable available size may replace the ordinary piece of film put behind a tooth or the teeth of a patient subject to X-ray examination. Such a CCD sensor adapted for X-ray radiation is for example marketed under the name SENS-A-RAY® and manufactured by Regam Medical Systems, Sundsvall, Sweden.

One very important result of this is that it is then possible to immediately obtain an image on a screen without the otherwise time consuming necessary chemical processing of the exposed X-ray film by developing it in a darkroom or within a special light sealed device.

Making use of the most recent state of the electronic art it is very advantageous to utilize some kind of computer equipment which is capable of receiving the electrical signals obtained from the CCD sensor when it is subjected to radiation by X-rays. Such a computerized equipment will have the potential to process the image data received from the CCD sensor to produce an image on a display as well as processing and storing images by means of standard mass storage devices. Such technique is for example disclosed in U.S. Pat. No 4,905,265 by Cox et al. 1990

In other words this technique will be extremely well suited for the using of a standard Personal Computer (PC) commonly found on the market, and manufactured by many different companies. Such a device will be able to perform all the wanted functions in this respect. However there is an obvious drawback as most of these devices will in reality not be permitted for use within an area of defined medical electric environment. In other words a Personal Computer used in such an environment must primarily fulfil the demands of the International Standard IEC 601-1 (second edition) which concerns medical electric equipment and the particular requirements for safety even if the used CCD sensor package itself is primarily nonconducting.

Thus this is the main obstacle to be able to use such inexpensive computer equipment in this application due to the demand of electric approval for the using of such electric or electronic devices within a medical electric environment. Standard PC:s does not possess such an approval as this implies additional costs in testing and production of the devices, which for standard computer use should result in too expensive equipment which will not be competitive in the general market. A series of such approved equipment for use within areas of medical electric environment will be small in quantity compared to standard equipment series and thus will be fairly expensive to the customer.

Consequently there is a high demand for a method and an apparatus to facilitate the use of common market standard personal computers for the displaying, processing and storing of images produced by CCD-sensors utilized for dental intraoral X-ray examinations. Such a system should still preferably rely on a base of wired connections to simplify the overall need of any additional equipment as well as simultaneously keep any induced interference to other adjacent equipments, such as radio receivers and the like, at a minimum.

DESCRIPTION OF THE INVENTION

There is then an object of the present invention to provide a method and an apparatus to facilitate feeding of electric signals, achieved in a defined area of medical electric environment, to and from equipment, specifically a so called Personal Computer (PC), without to necessitate that such an equipment itself must fulfil all the requirements necessary for use within said area of medical electric environment.

There is another object of the present invention by means of isolation means having its own power supply which according to the International Standard IEC 601-1 (second edition) is approved for use within an area of medical electric environment to provide an insulation between an area of medical and an area of nonmedical electric environment.

There is still another object of the present invention to by said isolation means, preferably positioned outside the defined area of medical electric environment, to provide an insulating interface to a CCD sensor within said area of medical environment for the transmission of electric signals from and to said CCD sensor to and from any electric or electronic facility such as a computer or the like outside said area of medical electric environment.

Yet another object of the present invention is to provide a multiline interface using discrete wires and/or optical fiber for parallel transmission of control signals to the CCD sensor and electric data signals or image signals from the CCD sensor while still maintaining the defined border between said area of medical electric environment and the other area of non-medical electric environment.

There is yet another object of the present invention to provide ment, such as a dentist's chair or the like, having just one cable of suitable length connecting, via said isolation means having its own protected power supply, to the outside area of non-medical environment where the display unit of the used standard PC presenting an image produced by the CCD sensor is positioned to be easy visible but not touchable by anyone or anything who may at the same time be in contact with a person subject to the CCD sensor during the treatment in a dentist's chair or the like.

BRIEF OF THE DRAWINGS

Below the invention will in detail be described by referring to the enclosed drawings in which.

DETAILED DESCRIPTION OF A PREFERRED EMBODIMENT

Figure 1:
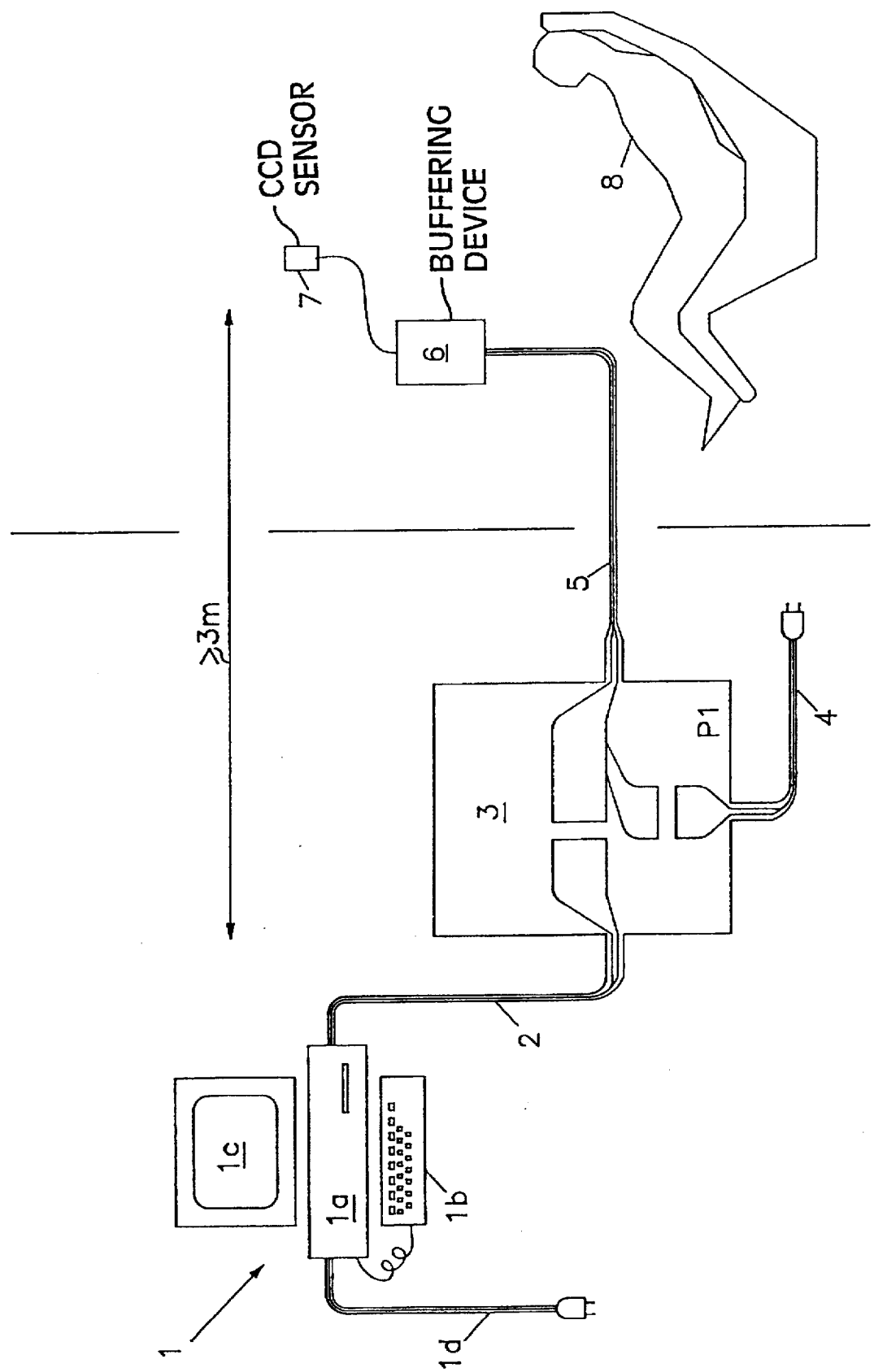
FIG. 1 is a general illustration according to the present invention, of a defined area of medical electric environment and an area of non-medical electric environment.

In FIG. 1 is demonstrated a preferred embodiment of the method and apparatus according to the present invention.

The right side of FIG. 1 represents a first area defined as medical environment containing a dentist's chair and a patient 8. The left side of FIG. 1 is showing a second area defined as non-medical environment and is primarily in the example embodiment containing an auxiliary equipment 1 constituting a standard Personal computer having a main unit 1a comprising a processor, work memory, storage facilities like a hard disc or a standard diskette station and a keyboard 1b and a display screen 1c. This computer is normally supplied by its own power cord 1d connected to a mains outlet. The computer 1 then constitutes equipment which most probably electrically is not approved for a medical environment and is therefore positioned at a security distance from the dentist's chair within the defined medical environment, for example, 3 meters to obtain a necessary safety distance. This distance between the equipment 1 and the person 8 in the dentist's chair, will imply that it is not possible for another second person, i.e. the dentist to simultaneously be in contact both with the equipment 1 and the patient 8.

For X-ray intraoral investigation of the patient's teeth the dentist wishes to make use of an CCD sensor 7 available within the defined area of medical environment. This CCD sensor 7, which in the preferred embodiment constitutes a SENS-A-RAY® sensor manufactured by Regam Medical Systems, Sundsvall, Sweden, has to communicate with the computer equipment 1 to be able to create an X-ray image on the display screen 1c by means of the computer. This can not be accomplished by Just connecting the CCD sensor 7 to the computer 1 as that would infer introducing the non-medical electric environment onto the medical electric environment surrounding the patient. Equipment which is supposed to be positioned within the defined medical environment should conform to the International Standard IEC 601-1, (second edition).

Therefore according to the present invention a secondary equipment forming an isolation unit 3 is introduced, which by a cable 2 is connecting the computer 1 to an isolation unit 3, and by another cable 5 is connecting the isolation unit to the CCD sensor 7, in a preferred embodiment of the present invention, through a buffering device 6. Additionally the isolation unit 3 is having its own power supply P1 connected to a wall outlet via a mains power cord 4. In the preferred embodiment this power supply is integrated with the rest of the isolation unit, but could of course form its own entity which may be battery powered or powered from a mains outlet. This power supply when using line power is designed by taking into account the Clause 14, regarding "Class II Equipment" as well as the Clause 19, regarding "Type BF Equipment" of the IEC 601-1 to facilitate a unit which from this point of view would be allowable inside the defined area of medical environment regarding the particular electric requirements for safety of a patient. In the preferred embodiment the case of the isolation unit 3 is a box of nonconducting material having no touchable metallic parts. Still according to the preferred embodiment of the present invention the isolation unit is preferably kept out of the defined area of medical environment.

Figure 2:
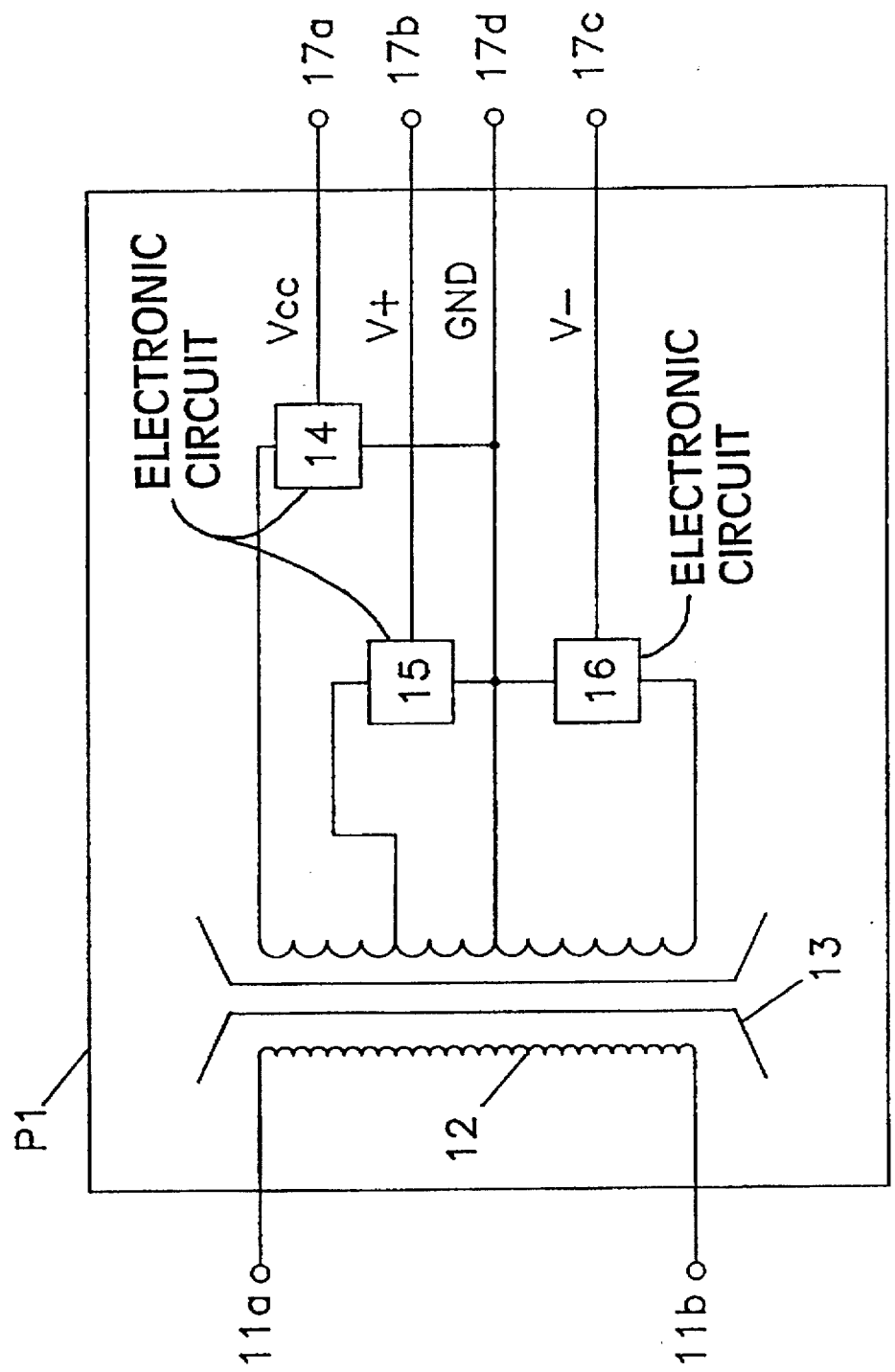
FIG. 2 is a block diagram of a power supply for connection to the public electric network according to a preferred embodiment of the present invention as illustrated in FIG. 1.

FIG. 2 is a simplified circuit diagram of the power supply P1 in the isolation box intended for the use of the public electric network, e.g., 115 or 230 V AC. The power supply P1 comprises according to already established technique a transformer 12 having its input terminals 11a and 11b connected to the power cord 4 preferably via a power switch and a built in fuse (not shown) and electronic circuits 14, 15 and 16 comprising standard rectifiers, resistors, capacitors and transistors or voltage stabilizing integrated circuits and producing the different voltages V+, V− and Vcc, respectively, at the outputs 17a through 17d of the power supply. These different voltages are partly used for one side of the signal isolation circuits within the isolation unit 3 as well as partly fed to the buffering device 6 and/or the CCD sensor 7. The different voltages V+, V− and Vcc, respectively, are referred to a floating ground reference GND forming terminal 17c. The transformer 12 in the preferred embodiment is additionally having an electrostatic screen 13 to capacitively further separate the primary and secondary circuits. The power supply P1 of the preferred embodiment is making use of transformers like type 8782- 0002 (230 V AC) or 8782- 0003 (115 V AC), manufactured by Tufvassons, Sigtuna, Sweden, and having insulation ratings of at least 4 kilovolts.

Figure 3:
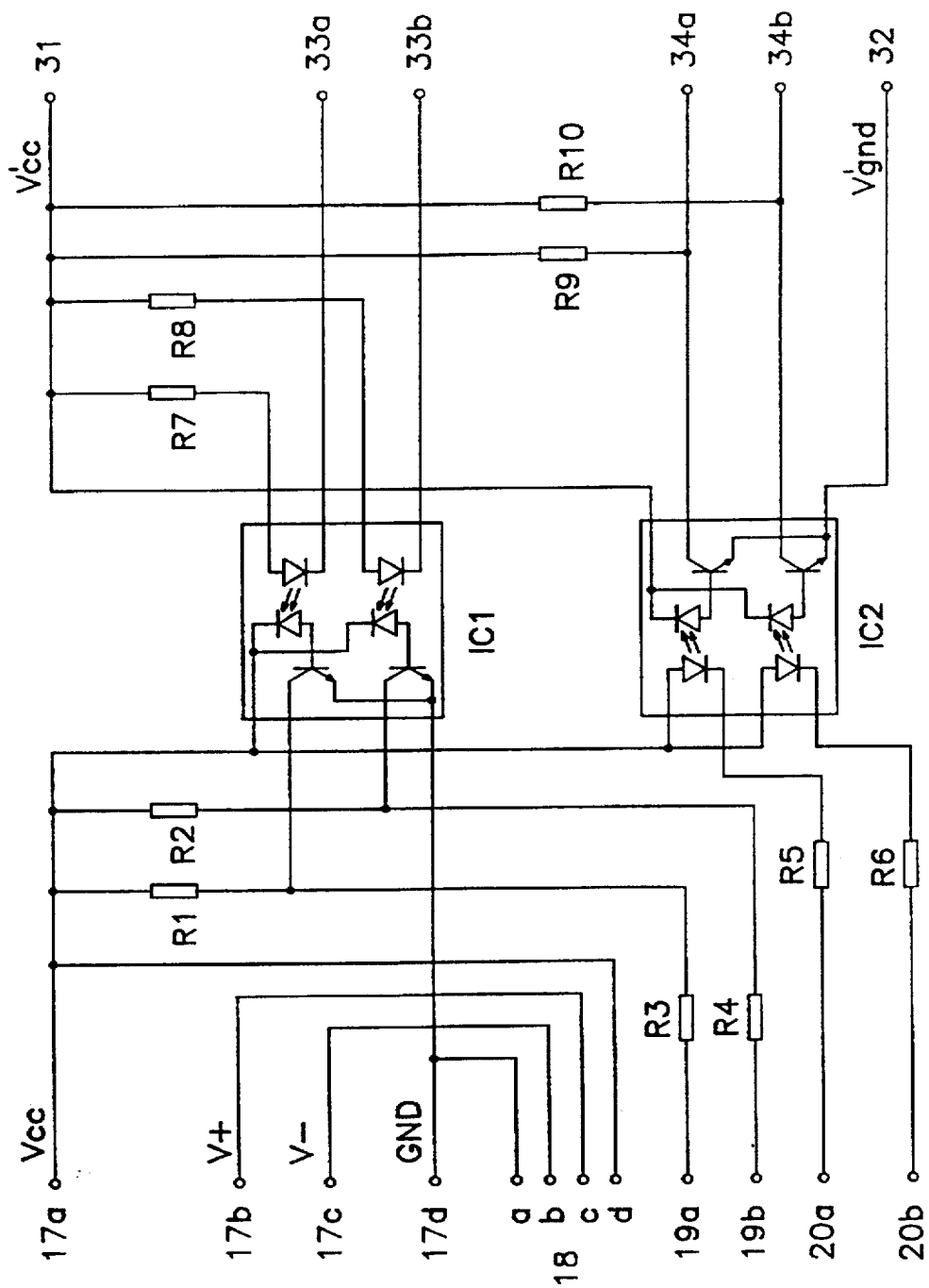
FIG. 3 is a portion of a circuit diagram concerning the isolation unit in FIG. 1 using optoelectric interfaces according to the present invention.

FIG. 3 is demonstrating a portion of the isolation circuitry of the isolation unit 3. The left side of this circuit represents the side connected to cable 5 in FIG. 1, while the right side of the circuit is connected to cable 2. The signal transmission devices in the preferred embodiment consist of optocouplers from which two sets are illustrated by IC1 and IC2, respectively. Integrated circuits IC1 and IC2 are optocouplers having insulating ratings of 3 kilovolts like HCPL2631, manufactured by Hewlet Packard.

The right side which is connected by cable 2 to the computer 1 (FIG. 1) is receiving adequate voltage from the computer interface as indicated by terminals 31 (V'cc) and 32 (V'gnd). Terminals 33a and 33b indicate signal routes from the computer 1 to the CCD sensor 7, while terminals 34a and 34b indicate signal routes from the CCD sensor 7 to the computer 1.

The left side of the schematic diagram indicates the terminals 17a–17d, (Vcc, V+, V−and GND) connecting to the power supply P1 (FIG. 2). Terminals 18a–d represent the supplying connections going out to the buffering device 6 and/or the CCD sensor 7. Terminal 19a and 19b represent signal routes from the computer 1 to the buffering device 6 and/or the CCD sensor 7, while terminals 20a and 20b being signal routes from the buffering device 6 and/or the CCD sensor 7 to the computer 1. The input terminals 33a and 33b from the computer 1 are current limited by resistors R7 and R8, respectively, and equally the input terminals 20a and 20b from the buffering device 6 and/or CCD sensor 7 are current limited by resistors R5 and R6, respectively. Resistors R1 and R2 serve as pull-up resistors at the outputs 19a and 19b of IC1, while R9 and R10 serve as pull-up resistors at the outputs 34a and 34b of IC2. Resistors R3 and R4 constitute current limiting resistors for the output terminals 19a and 19b of IC1. In the preferred embodiment resistors R1 through R10 are standard ⅛ W resistors of 390 ohms. The arrangement of resistors is a function of the logic levels expected at the computer 1, respectively the buffering device 6 and/or the CCD sensor 7.

In the preferred embodiment all signals are transferred in parallel. This is accomplished by providing sixteen optocoupled channels in the isolation unit of which 4 channels are in the direction from the computer towards the CCD sensor for control and 12 channels are in the direction from the CCD sensor towards the computer carrying for example image information. Still any number of channels may be utilized. In a second embodiment where serial transmission is utilized which normally requires only one channel in each direction, but increasing the complexity especially of the buffering device 6 as well as the interface of the used SENS-A-RAY® sensor built into the computer 1. This built in specially designed interface normally utilizes parallel communication.

In a third embodiment a combination of wires and optical fibers is utilized resulting in extremely good signal transmission capabilities using serial or parallel transmission, but also at the cost of complexity of both the buffering device as well as the isolation unit. In the preferred embodiment the buffering device comprises simple integrated buffer circuit known to a person skilled in the art and are not further discussed. The buffering device creates primarily an interface to the more flexible cable used between the buffering device 6 and the CCD sensor 7 as this is a thin cable of a short but convenient length. In the cable 5 of the preferred embodiment each wire is separately shielded to obtain good crosstalk characteristics as this cable will be of a significant length when considering the parallel signal transmission. The strategy of using a buffering device and utilizing a more heavy cable from the buffering device to the isolation unit which then may be positioned at the most suitable place is considered the best mode of operation. Integrating the power supply P1 and the isolation unit 3 reduces the cabling to minimum.

By the arrangement thus disclosed cable 2 is insulated from cable 5 in the sense of ohmic contact signal routes and simultaneously also cable 5 is insulated in the sense of ohmic contact from cable 4 connected to the mains power. This is also indicated by the gaps in the electric routes in the illustration of the isolation unit 3 in FIG. 1. The arrangement provides the possibility to use equipment like the computer 1 connected to electric or electronic equipment within the medical environment without corrupting the medical electric environment and consequently any inexpensive computer equipment may be used for the processing, displaying and storing of image data from the CCD sensor 7 used for dental X-ray intraoral examination. Remote control of the computer may additionally easily be obtained using for example standard ultrasonic or IR equipment, whereby the most important basic functions of the computer easily will correspond to just the pressing of a single knob.

I claim:

1. A method for floating an encapsuled X-ray sensing device, used in a room for dental or medical care, from auxiliary electric equipment, not approved for use within a medical electric environment, for creating an image which is displayed by a display device of said auxiliary electric equipment, said image visualizing data from a CCD sensor in the encapsulated X-ray sensing device, comprising the steps of:

defining a first area of medical electric environment having therein a CCD sensor, and defining a second area of non-medical electric environment having therein auxiliary electric equipment not approved for use within said first area of medical electric environment, said second area of non-medical electric environment being spaced from said first area of medical electric environment at least by a distance which makes it impossible for a first person within said first area of medical electric environment to simultaneously touch said auxiliary electric equipment of said second area of non-medical electric environment and a second person subject to medical or dental care within said first area of medical electric environment, providing an isolation means enclosed in a separate box for electrically floating said CCD sensor, said isolation means being powered from standard mains by a transformer which together with additional electronic components forms a separate protected power supply which is approved for said first area of medical electric environment, providing a first cable for connection of said CCD sensor to said auxiliary electric equipment, a buffering device being connected to said first cable between said CCD sensor and said isolation means, providing a second cable for connection of said isolation means to said auxiliary electric equipment, providing protected supply voltages from said power supply to said buffering device and said CCD sensor, and providing non-ohmic contact interfacings within said isolation means between said first cable and said second cable utilizing electromagnetic and/or optoelectric components for transmission of electrical signals carried by said first cable and said second cable, respectively.

2. The method according to claim 1, including the further step of providing a length of said first cable from said buffering device to input terminals of said isolation means to be able to position said isolation means outside said first area of medical electric environment.

3. The method according to claim 2, further including the step of providing numerous shielded wires within said first cable and second cable and at least a corresponding number of non-ohmic interfaces within said isolation means to provide parallel transmission of control signals to said buffering device and to said CCD sensor as well as data signals forming image information from said CCD sensor to said auxiliary electric equipment for processing, displaying and storing image information.

4. The method according to claim 1, including the further step of providing numerous shielded wires within said first cable and second cable and at least a corresponding number of non-ohmic interfaces within said isolation means to provide parallel transmission of control signals via said buffering device to said CCD sensor and data signals forming image information from said CCD sensor to said auxiliary electric equipment for processing, displaying and storing X-ray image information.

5. An apparatus for separating auxiliary electric equipment from an encapsulated X-ray sensing device containing a CCD sensor used in a room for dental or medical care forming a first area of medical environment for creating an X-ray image which is displayed by a display device belonging to said auxiliary electric equipment, specifically a Personal Computer or the like, not approved for use within said first area of medical electric environment, comprising, a CCD sensor positioned in a first area of medical electric environment isolation means enclosed in a separate box for isolating said CCD sensor from auxiliary electric equipment positioned in a second area of non-medical electric environment, said isolation means having a power supply which is approved for a medical electric environment, a first cable and a second cable, said first cable having a first end connected to an electronic buffering device, said electronic buffering device being connected to said CCD sensor, a second end of said first cable being connected to a first side of said isolation means, a second side of said isolation means being connected to a first end of said second cable and a second end of said second cable being connected to said auxiliary electric equipment for transferring electrical signals from said CCD sensor to said auxiliary electric equipment.

6. The apparatus according to claim 5, wherein said isolation means produces protected supply voltages for said buffering device and said CCD sensor, and said isolation means offers electrically floating inputs and outputs for said first cable interfaces between said first cable and said second cable, thereby forming a non-ohmic link between areas of medical and non-medical electric environment, respectively.

7. The apparatus according to claim 6, wherein said first and second cables include numerous shielded wires to facilitate parallel signal communication between said CCD sensor and said auxiliary electric equipment, said first cable being of a length to permit positioning of the isolation means outside said first medical electric environment.

8. The apparatus according to claim 7, wherein said isolation means comprises a transformer according to a second edition of International Standard IEC 601, regarding protection against electric shocks, hazards and continuous leakage currents and wherein said transformer provides an electrostatic screen between primary and secondary windings.

9. The apparatus according to claim 6, wherein a part of said first cable includes at least one optical fiber to facilitate high speed signal communication between said CCD sensor and said auxiliary electric equipment, said first cable being of a length to permit positioning of the isolation means outside said first medical electric environment.

10. The apparatus according to claim 9, wherein said isolation means comprises a transformer according to a second section of International Standard IEC 601, regarding protection against electric shock, hazards and continuous leakage current and wherein said transformer provides an electrostatic screen between primary and secondary windings.

11. The apparatus according to claim 6, wherein said isolation means comprises a transformer according to a second edition of International Standard IEC 601, regarding protection against electric shocks, hazards and continuous leakage currents and wherein said transformer provides an electrostatic screen between primary and secondary windings.

12. The apparatus according to claim 5, wherein said isolation means comprises a transformer according to a second edition of International Standard IEC 601, regarding protection against electric shocks, hazards and continuous leakage currents and wherein said transformer provides an electrostatic screen between primary and secondary windings.

13. An apparatus for insulating an X-ray sensing device containing a CCD sensor from auxiliary electric equipment, comprising:

an X-ray sensing device containing a CCD sensor positioned in a first area which defines a medical electric environment;

auxiliary electric equipment positioned in a second area which defines a non-medical electric environment;

isolation means, enclosed in a separate box and containing isolation circuitry having a first side, a second side and a power supply approved for a medical electric environment, for electrically floating said CCD sensor, a first cable extending from one first cable end, connected to said second side, to an opposite first cable end connected to said CCD sensor; and a second cable extending from one second cable end, connected to said first side, to an opposite second cable end connected to said auxiliary equipment.

14. The apparatus of claim 13 further including an electronic buffering device connected to said first cable between said second side and said CCD sensor.

* * * * *